United States Patent [19]

Shu et al.

[11] 4,211,238
[45] Jul. 8, 1980

[54] APPARATUS AND METHOD FOR RECORDING AND PLAYING BACK ELECTROCARDIAL SIGNALS

[75] Inventors: Stephen K. Shu, Fountain Valley; W. David Squires, Huntington Beach, both of Calif.

[73] Assignee: Del Mar Avionics, Irvine, Calif.

[21] Appl. No.: 918,698

[22] Filed: Jun. 23, 1978

[51] Int. Cl.² ............................................. A61B 5/04
[52] U.S. Cl. ................................... 128/700; 128/711; 346/33 ME
[58] Field of Search .................... 128/2.05 Q, 2.05 R, 128/2.06 B, 2.06 G, 2.06 R, 2.1 A; 346/33 ME

[56] References Cited

U.S. PATENT DOCUMENTS

| | | | |
|---|---|---|---|
| 3,572,316 | 3/1971 | Vogelman et al. | 128/2.05 R |
| 3,830,228 | 8/1974 | Foner | 128/2.06 R |
| 3,946,744 | 3/1976 | Auerbach | 128/2.06 A |
| 4,006,737 | 2/1977 | Cherry | 128/2.06 G |
| 4,033,336 | 7/1977 | Murawski et al. | 128/2.05 R |
| 4,073,011 | 2/1978 | Cherry et al. | 128/2.06 G |

OTHER PUBLICATIONS

McKinnon, "Proceedings of Biotelemetry II 2nd International Symposium," Davos Switzerland, 20–24, May 1974, pp. 67–70.

*Primary Examiner*—William E. Kamm
*Attorney, Agent, or Firm*—Smyth, Pavitt, Siegemund, Jones & Martella

[57] ABSTRACT

A system for encoding, recording, playing back, decoding, validating, and displaying cardiac signals obtained from a patient during ambulatory monitoring. The system permits the recording on a single track in a magnetic tape of a channel of ECG signals interrupted intermittently by blood pressure signals, time of day signals, and event marker signals. The ECG signal is recorded in analog form, but the other signals are recorded as pulse coded signals each having its own format. In the playback apparatus, decoders identify and verify each of the signals when they occur, and the played back information is plotted on a chart. If the time of day signal was not recorded on the tape, timing information can be produced by the playback apparatus from the cumulative tape travel. Fiducial signals introduced in the recording, playback, and charting operations are used in a method for identification and measurement of recording tape speed error, playback tape error, and plotter speed error.

42 Claims, 4 Drawing Figures

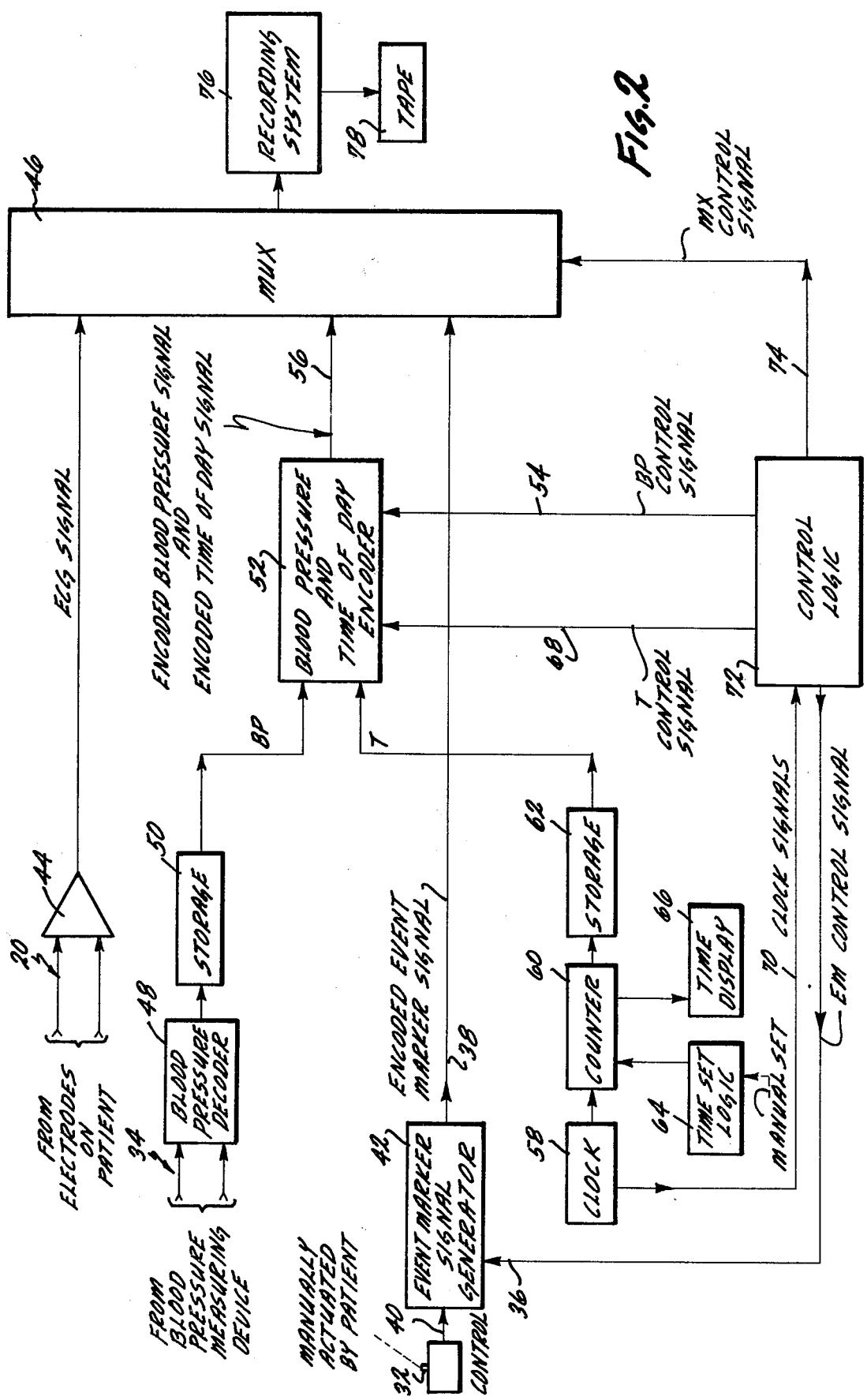

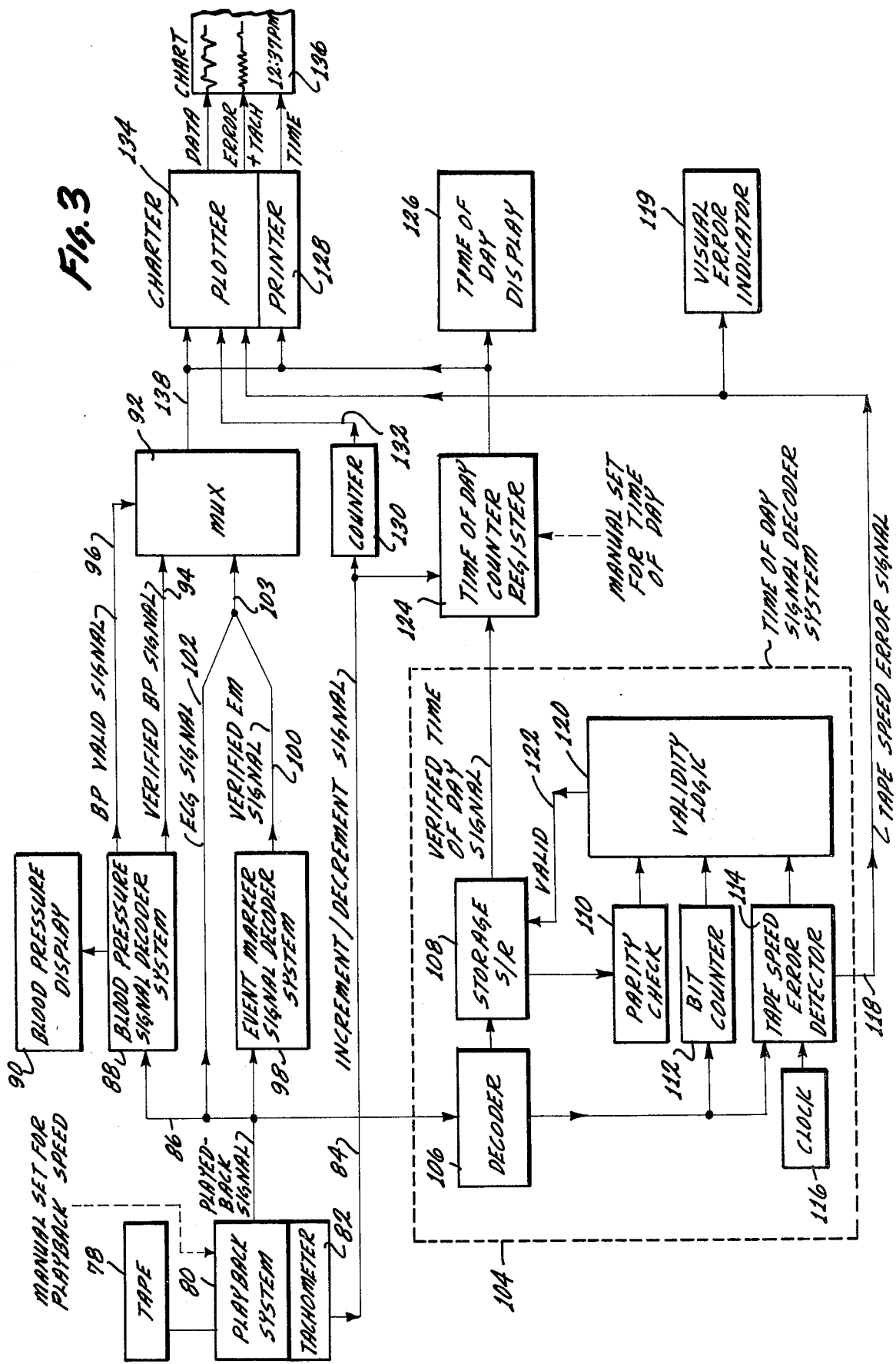

APPARATUS AND METHOD FOR RECORDING AND PLAYING BACK ELECTROCARDIAL SIGNALS

BACKGROUND OF THE INVENTION

1. Field of the Invention

The present invention is in the field of electrocardiography and more specifically relates to apparatus for encoding, recording, playing back, decoding and displaying cardiac data, including selected ECG signals and blood pressure data.

2. The Prior Art

The present invention is a further step forward in the continuing development of instruments for ambulatory (Holter) monitoring. The present invention is in the nature of an innovative combination of certain prior art techniques, combining them with new techniques to obtain a new and useful result. For this reason, a knowledge of the salient prior art techniques is essential for understanding the present invention and viewing it from the proper perspective.

The U.S. Pat. No. 4,006,737 issued Feb. 8, 1977 to Cherry and assigned to Del Mar Engineering Laboratories, there was described an electrocardiographic computer for playing back, analyzing and displaying ECG signals recorded on a magnetic tape. Two channels of ECG signals are recorded on separate tracks in the magnetic tape. The recorder is not disclosed.

The electrocardiographic computer described in U.S. Pat. No. 4,006,737 includes provision for playing back the tape at a high speed so that the data may be quickly scanned by a skilled operator to determine which portions are significant. The electrocardiographic computer further includes provision for replaying at real time speed the portions of the tape deemed to be significant. When the tape is scanned at high speed, the computer calculates and continuously plots two channels of trend data such as heart rate and ST level. An arrhythmia computer within the electrocardiographic computer detects and digitally displays the number of premature ventricular contractions and the number of supraventricular ectopic beats and actuates an event marker to place a mark on the chart produced when the arrhythmia occurrences exceed a preselected number of occurrences during a predetermined time interval. When the tape is replayed at real time speed, the two channels of ECG data ae plotted. A printer indicates the time of day on the chart, but this time of day data is based on the amount of tape that has been played, as sensed by a tachometer system within the electrocardiographic computer.

U.S. Pat. No. 4,073,011 issued Feb. 7, 1978 to Cherry and Anderson describes an improved electrocardiographic computer as well as a recorder. The recorder again employs two tracks for recording on the tape. One channel of ECG signals is recorded on one of the tracks, while on the other track is recorded the second channel to ECG signals interrupted intermittently by event marker signals initiated by the patient. The recorder includes a time display so that the patient can note the time at which he initiated the event mark.

The electrocardiographic computer described in U.S. Pat. No. 4,073,011, on which the tape is played back, differs from the computer described in U.S. Pat. No. 4,006,737 in a number of improvements which cumulatively provide for a much greater degree of automatic processing of the tape so that the monitoring of the tape may be accomplished without the necessity of a technician's visually observing the oscilloscope or listening to an audible representation of the ECG signals. For example, during playback, the computer may be set to provide a trend run so as to print out a trend analysis from the beginning to the end of the tape and then have the tape stop automatically. Thereafter, the computer can be set to automatically cycle to the beginning of the tape to again print out the trend analysis but with an automatic detection of various events. The detection of the various events is used to trigger the computer so that the tape is slowed down to real time to print out the portion of the ECG signals bearing on the event. Thus, the technician does not have to monitor the playback to manually slow the tape down to real time as was done in the prior computer, but instead, the computer itself senses the occurrence of an event during trend and slows the tape down to print out in real time the ECG signals and then speeds back up to the orginally-selected trend speed.

The chart produced by the computer of U.S. Pat. No. 4,073,011 is the same as that produced by the computer of U.S. Pat. No. 4,006,737 during high-speed scan, but during real time playback the event marker signal initiated by the patient is displayed on one of the EGC traces in the computer, as described in U.S. Pat. No. 4,073,011.

In application Ser. No. 796,893 filed May 16, 1977 for "Blood Pressure Monitoring System," by Squires et al., there is disclosed a blood pressure measuring apparatus suitable for long-term ambulatory monitoring of the blood pressure of the patient to whom the device is affixed. The blood pressure measuring device is used in conjunction with a recorder of the type described in U.S. Pat. No. 4,073,011, with certain modifications made to the recorder. One of the modifications establishes the priority of the signals for recording. The recorder is capable of recording on two tracks of the tape simultaneously, and one of the tracks is dedicated to a first channel of ECG signals. On the second track of the tape a second channel of ECG signals is recorded, but is interrupted intermittently by the patient-initiated event marker signal and by the intermittently-generated blood pressure data signal. The blood pressure data signal has first priority followed by the event marker signal, and the lowest priority is given to the second channel of ECG signals.

The tape produced by the recorder used in conjunction with the blood pressure measuring apparatus is intended to be played back on the electrocardiographic computer described in U.S. Pat. No. 4,073,011 with slight modifications. That computer, as modified, permits a mark representing the blood pressure measurement to be placed on the heart rate trend chart during playback at ×60 and ×120 speeds, as shown in FIG. 15 of the application Ser. No. 796,893.

In the recorder described in U.S. Pat. No. 4,073,011, and used in the blood pressure apparatus, the event marker signal consists of a burst of eight cycles at a frequency of 8 Hz. When used in conjunction with the blood pressure measuring apparatus of Ser. No. 796,893, the recorder is modified to include a blood pressure encoder which encodes the systolic and diastolic blood pressure readings in a form particularly well suited for recording and subsequent decoding. The systolic reading includes eight binary bits and the diastolic reading includes another eight binary bits, so that the entire signal consists of sixteen bits which are produced at the rate of 16 Hz. The sixteen-bit blood pressure signal is preceded and followed by a one-eighth-second blanking preamble and postamble.

When used to play back tapes made in conjunction with the blood pressure measuring apparatus, the computer described in U.S. Pat. No. 4,073,011 is modified to include a decoder for decoding the blood pressure signal, which can be identified in that it consists of sixteen pulses at a 16-Hz rate.

The portable tape recorder disclosed in U.S. Pat. No. 4,073,011 and modified as described in application Ser. No. 796,893 to permit both an encoded blood pressure signal and an event marker signal to be placed on one of the tracks along with the ECG signal, is further modified and improved in the present invention, as will be described below. Likewise, the electrocardiographic computer described in U.S. Pat. No. 4,073,011 and modified as described in application Ser. No. 796,893 to provide for decoding of the blood pressure signal is further modified and improved in the present invention, as will also be described below. For these reasons, the descriptions given in U.S. Pat. No. 4,073,011 and application Ser. No. 796,893 filed May 16, 1977 are deemed to be incorporated herein for purposes of disclosure and to avoid unnecessary repetition of the background material.

In the recorder and the electrocardiographic computer described in U.S. Pat. No. 4,073,011 and in application Ser. No. 796,893, a magnetic recording tape of a standard width is used, and two tracks of data are recorded on it. This type of tape and the two-track recording format has become relatively standard and use of the electrocardiographic computers and recorders has become widespread.

For this reason, it was deemed essential that the apparatus of the present invention must be compatible with the equipment already in widespread use. Thus, it was essential that the apparatus of the present invention employ a magnetic tape of the same standard width and having two data tracks recorded on it. It was also deemed essential that the recorder of the present invention be usable to record the data in a form which can be analyzed with the existing electrocardiographic computers so far as possible, and that the electrocardiographic computer when modified in accordance with the present invention must still be able to play back and analyze tapes made on existing recorders.

In the electrocardiographic computers described in U.S. Pat. Nos. 4,006,737 and 4,073,011, the electrocardiographic computer kept track of the time of day at which the signals occurred through the use of a tachometer system driven by the tape as it is played back. In that system, the tape engages a capstan which produces rotation of an optical encoder which produces a biphase electrical pulse each time the tape has travelled an additional one-sixteenth inch. These tachometer pulses are used to increment a counter into which it was necessary for the operator to insert time of day.

It has been found from experience that the rubber portion of the capstan which engages the magnetic tape has a tendency to age and to wear with extended use. This, combined with friction in the tape path results in tape speed errors which are cumulative, and during a twenty-four-hour recording session, a one-percent change in tape speed will produce an accumulated error of fourteen minutes.

Thus, the present invention arose from the need to find a better way of determining the time at which the recorded signals occur, but as described above, it was recognized that whatever solution was implemented would have to be compatible with existing equipment.

SUMMARY OF THE INVENTION

The present invention solves the problem of how to record a continuous ECG channel as well as intermittent blood pressure, event marker and time of day signals on a single track of a magnetic tape in such a way that the data can be recovered by existing playback and analysis equipment with a mininum of modification and to that the tapes produced by existing recorders can be played back and analyzed by the playback and analysis system used in the present invention.

Accordingly, in the present invention, the standard tape width and two-track recording format is retained. As in the previous systems, one of the tracks is dedicated to a first channel of ECG signals. On the second track, a second channel of ECG signals is recorded, interrupted by the intermittent presence of blood pressure, event marker and time of day signals. The time of day signals are generated each minute on the minute with great precision and the blood pressure and event marker signals occur intermittently. The recording priority system utilizes storage to delay recording of a blood pressure signal until immediately following the next-occurring time of day signal. Also, generation of the event marker signal is delayed if the patient initiates the signal when other signals are to be recorded.

Thus, the recording priority scheme used in the present invention and enabled by the coding system used permits prompt recording of each of the intermittent signals while at the same time keeping interruptions of the ECG signal to a minimum.

In accordance with the present invention, a time of day signal is recorded in a fourteen-bit phase mark code on the second track on the magnetic tape along with the event marker signals, the blood pressure signals and the ECG signal. The fourteen bits are generated at a frequency of 21.33 Hz and the time of day signal is preceded by a three-bit preamble and is followed by a two-bit postamble. The last of the fourteen bits is a parity check bit used for validating the decoded time of day signal.

Because the time of day is recorded on the tape along with the other signals, the problem of cumulative speed error inherent in the tachometer time keeping system of the previous systems is overcome. Further, because the time of day is recorded on the tape in the present invention, it is not necessary for the operator to set into the playback equipment an initial time of day.

Moreover, the patient does not have to be concerned about noting the time of day or night at which various events occur.

The tapes recorded in accordance with the present invention are compatible with existing playback equipment such as that described in U.S. Pat. No. 4,073,011 and in application Ser. No. 796,893 in the sense that the time of day signals recorded on the tape will simply be ignored by the existing playback units which will determine the time of day by the tachometer technique.

To insure compatibility of the playback equipment of the present invention with tapes recorded on existing equipment, the tachometer system is retained in the present invention. When tapes recorded on existing equipment are played in the playback system of the present invention, time of day is determined by the tachometer method. However, when tapes recorded in accordance with the present invention are played back on the playback system of the present invention, the time of day determined by the tachometer system is overruled by the time of day reproduced from the tape.

In addition to assuring full compatibility with existing equipment, the system of the present invention results in two previously-unexpected advantages.

The phase mark pulse code employed in the present invention enjoys a high degree of noise immunity. Spurious signals are discarded by the decoder, permitting the system to operate properly in spite of high noise levels such as might be produced by poor electrode contact or by muscular contractions. The decoder system can operate satisfactorily with as much as ninety percent of the signal dropped out. Only positively identified signals are passed on as valid to the plotter.

A second major advantage of the system of the present invention is its ability to permit identification and measurement of recording tape speed errors, playback tape speed errors, and charter speed errors. In producing this new result, the tachometer in the playback portion of the present invention performs additional functions compared to the manner in which it was used in the prior art.

The determination of the recorder speed error, the playback speed error and the charter speed error is enabled in the present invention by causing the charter to plot on the chart three different types of signals. First, the successive time of day signals generated by a crystal-controlled clock in the recorder are plotted on the chart. Because these signals are produced in the recorder are recorded and then played back and charted, the spacing between the successive time of day signals on the chart is affected by the recording speed error, by the playback speed error and by the charter speed error.

The second type of signals plotted on the chart are tachometer pulses which are generated in the playback equipment by the movement of the tape. On the chart, the tachometer signal has the form of a succession of individual pulses spaced approximately five seconds apart. Clearly, the spacing on the chart between successive tachometer pulses is affected by the playback speed error and the chart speed error, but not by the recording speed error. Thus, the recording speed error can be determined by subtracting the error determined from the tachometer pulses from the error determined from the time of day signals.

According to the present invention, the decoder used to identify and verify the time of day signals includes a tape speed error detector which detects the net sum of the recording speed error and the playback speed error. When this sum exceeds a predetermined value, the time of day decoder generates a tape speed error signal which is plotted on the chart. The tape speed error signal consists of a burst of pulses at a 20 Hz rate, and this rate is accurately controlled. Thus, the tape speed error signal has a known duration in time, and accordingly, the interval on the chart between the beginning and the end of the tape speed error signal permits the charter speed error to be determined. The playback speed error is then determined by subtracting the charter speed error from the error derived from the tachometer pulses, which, it will be recalled, included both the playback speed error as well as the chart speed error.

The various speed errors may also be determined according to the present invention when the tape speed error signal is not generated; that is, when the recording speed error is offset by a playback speed error of equal magnitude but opposite sense. In this case, the distance on the chart between successive time of day signals is affected only by the charter speed error, and therefore the charter speed error can be determined from the distance between the successive time of day signals on the chart. Nevertheless, the distance between successive tachometer pulses on the chart continues to be affected by both the playback speed error and the charter speed error. Therefore, the playback speed error can be determined by subtracting the error determined from the successive time of day signals on the chart from the error determined from the successive tachometer pulses on the chart. In this case, the recording speed error is, by assumption, of equal magnitude and opposite sense to the playback speed error.

The ability to determine the various speed errors affecting the signals plotted on the chart is important, since the chart paper used by the plotter is supplied with a gridwork printed on it corresponding to specific time increments. Further, the determination of the various speed errors is of great value in setting up and maintaining adjustment of the apparatus, and permits corrective measures to be taken to adjust the speeds to their proper values.

The ability to identify and measure the various speed errors is a new and unexpected result made possible by recording the time of day signal and by generating the tape speed error signal in the present invention, and this capability is not present in the previous equipment described in U.S. Pat. No. 4,073,011 and in application Ser. No. 796,893, referred to above.

The novel features which are believed to characterize the invention, both as to its organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is a block diagram of the tape recorder of the present invention showing the encoding and recording systems;

FIG. 3 is a block diagram of the decoder of the present invention showing the playback, decoding and display systems.

DESCRIPTION OF THE PREFERRED EMBODIMENT

Figure 1:
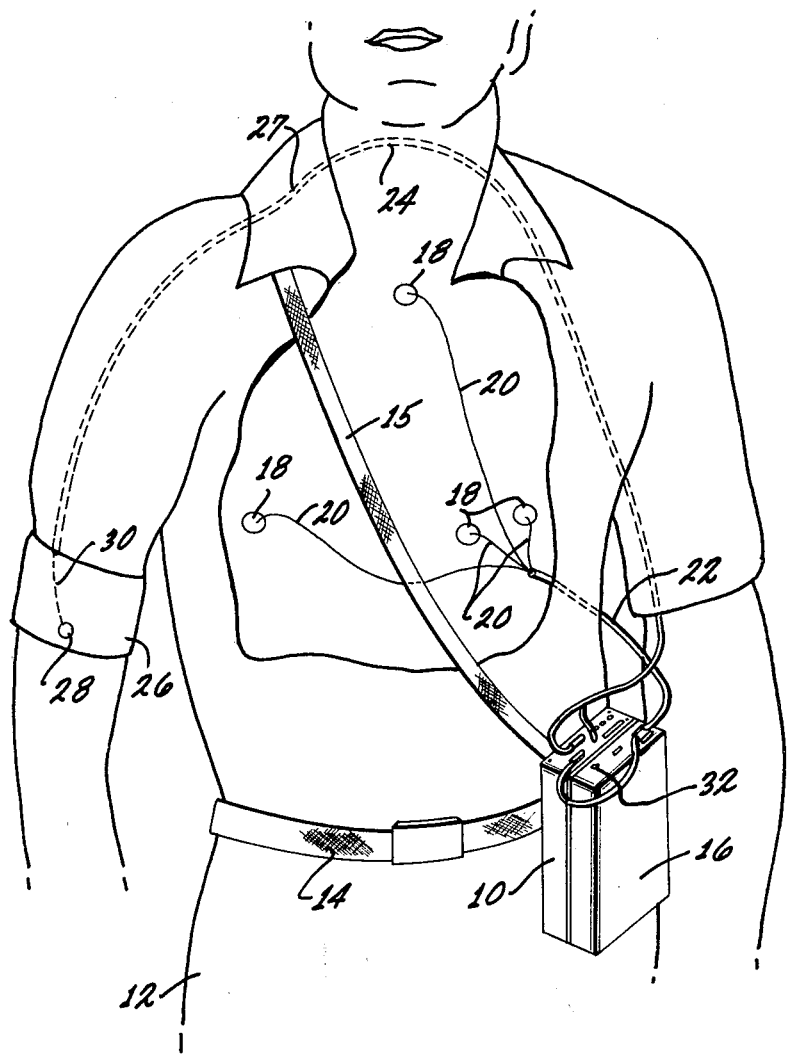
FIG. 1 is fractional perspective view showing the blood pressure measuring apparatus and the recorder affixed to a patient.

Turning now to the drawings, in which like parts are identified by the same reference numeral, there is shown in FIG. 1 the blood pressure measuring apparatus 10 and the portable tape recorder 16 of the present invention affixed to the patent 12 by a belt 14 around the patient's waist or by a strap 15, which extends in a loop over a shoulder of the patient 12. The portable tape recorder 16 is affixed to the blood pressure measuring apparatus 10 for convenience. A number of ECG electrodes 18 are affixed to the body of the patient 12 in the usual manner in which such electrodes are attached. The lead wires 20 from the ECG electrodes are formed into a cable 22 which is attached to the recorder 16.

A hose 24 extends from the blood pressure measuring apparatus 10 over the shoulders of the patient 12 to a pressurizable cuff 26 which is affixed to the upper portion of the patient's arm. The hose 24 carries the air used for inflating the cuff 26. A microphone 28 is positioned between the pressurizable cuff 26 and the patient's arm near the distal edge of the cuff 26, as shown in FIG. 1. The microphone 28 converts the Korotkov sounds to electrical signals which are conducted through the microphone cable 30 to the blood pressure measuring apparatus 10.

The blood pressure measuring apparatus 10 and the portable tape recorder 16 operate from a self-contained power supply capable of powering those units for monitoring sessions for as long twenty-six hours. The portable tape recorder 16 records on a magnetic tape driven continually at a relatively slow speed, so that a single tape is adequate to store twenty-six hours of data. In the preferred embodiment, the tape recorder 16 is capable of recording simultaneously on two separate tracks of the magnetic tape. When sufficient data has been accumulated, the magnetic tape may be removed from the recorder 16 for playback.

In accordance with the preferred embodiment of the present invention, one of the two recording tracks of the magnetic tape is dedicated to recording a first channel of ECG signals. No other signals are recorded on that track, so that an uninterrupted ECG signal is available at all times during the monitoring period.

On the second track of the magnetic tape there is recorded a second channel of ECG signals, but this second channel of ECG signals is interrupted by recording on the same track of several intermittent signals including blood pressure signals received intermittently from a portable blood pressure measuring device affixed to the patient, by an event marker signal generated in response to actuation of an event marker control from time to time by the patient, and by a periodically recurring time of day signal.

The blood pressure measuring device 10 is shown in detail in U.S. patent application Ser. No. 796,893, filed May 16, 1977, for "Blood Pressure Monitoring System." The disclosure of that application is incorporated herein by reference. For present purposes, it is sufficient to know that the blood pressure measuring device takes the patient's blood pressure typically every fifteen minutes, and both the systolic and diastolic pressures are determined by an auscultatory technique. The systolic pressure reading is stored for readout in the blood pressure measuring device as an eight-bit binary word; likewise, the diastolic blood pressure reading is also stored for readout within the blood pressure measuring device as an eight-bit binary word. The stored blood pressure readings are read out in a serial bi-phase mark pulse code format including a one-eighth-second blanking preamble followed by the sixteen-bits at a frequency of 16 Hz followed by a one-eighth-second postamble. This signal is one of the inputs to the recorder of the present invention and it is applied to the input lines 34 of FIG. 2.

The portable tape recorder 16 shown in FIG. 1 is similar to that described in U.S. Pat. No. 4,073,011 except for the modifications thereto described herein. In particular, the event marker signal generator and its control 32 of FIGS. 1 and 2 are substantially the same as disclosed in application Ser. No. 796, 893 referenced above, except as noted below.

When the patient experiences a sensation which he regards as significant, the patient actuates the control 32 which, as may best be seen by reference to FIG. 2, produces an enabling signal on the line 40 to the event marker signal generator 42. In accordance with a preferred embodiment of the present invention, the event marker signal generator 42 does not begin to generate the encoded event marker signal on the line 38 until it has received an enabling signal on the line 36, which will be described below. Upon receipt of enabling signals on both the lines 36, 40, the event marker signal generator 42 generates an event marker signal consisting of eight cycles of a square wave at a frequency of 8 Hz. This burst of eight cycles will then be recorded on the magnetic tape in lieu of the ECG signal normally being recorded on the second track of the tape.

As shown in FIG. 2, the ECG signal from the lines 20 are amplified by the amplifier 44 and then applied to an input terminal of the multiplexer 46. As disclosed in application Ser. No. 796,893, the amplifier 44 includes two stages of amplification and a pre-emphasis filter network.

The serial phase mark pulse coded blood pressure readings received on the input lines 34 from the blood pressure measuring device 10 may not be recorded immediately, as will be described below, and therefore must be stored temporarily. The blood pressure decoder 48 thus converts the phase mark coded data into binary coded data for storage in the storage register 50.

The blood pressure encoder system includes the blood pressure decoder 48, the temporary storage 50 and the encoder 52. In a preferred embodiment, the encoder 52 upon receipt of a BP control signal on the line 54 clocks the stored data out of the storage register 50, encodes it back into serial bi-phase mark pulse coded form and applies it via the line 56 to an input terminal of the multiplexer 46.

Thus, the present invention differs from that described in application Ser. No. 773,618 in that the blood pressure data is not recorded immediately on the tape, but instead is temporarily stored until called forth by means of a BP control signal. Temporary storage of the blood pressure signal is necessary in accordance with the recording priority system employed in the present invention, as will be discussed below.

The recorder of the present invention further includes a time of day encoder system which includes the clock 58, the counter 60, the temporary storage 62 and the encoder 52, the latter being the same encoder used for encoding the blood pressure signals, in a preferred embodiment.

The clock 58 is crystal-controlled and its output signal is fed to a counter 60 which, as is well known in the art, functions to divide the frequency of the clock-produced signal and serves to store the accumulated count which indicates the time of day once a starting value has been inserted into the counter through the time set logic 64. The time of day is displayed on the time display 66 and is stored in the storage register 62 which typically is a part of the counter 60.

Upon receipt of a T control signal on the line 68, the encoder 52 clocks out the stored time of day from the storage register 62, converts it to a serial phase mark format and applies it via the line 56 to an input terminal of the multiplexer 46.

The clock 58 also supplies clock signals via the line 70 to the control logic 72 which produces a MX control signal on the line 74 for controlling the operation of the multiplexer 46 to insure that only one of the four signals (ECG, blood pressure, time of day, and event marker) is recorded on the second track of the tape at any time.

The control logic 72 implements the recording priority scheme used in accordance with the present invention. The T control signal on the line 68 is obtained by division of the frequency of the clock signal applied to the control logic 72 on the line 70. Thus, the time of day signal is recorded regularly every minute on the minute without regard for any of the other signals, and thus, the time of day signal enjoys the highest priority.

The second highest priority is given to the blood pressure signals and this is implemented in the control logic 72 by inhibiting production of the BP control signal at all times except during a brief interval beginning at the termination of the T control signal. Thus, regardless of when a set of blood pressure readings is received from the blood pressure measuring device on the input lines 34, the data is stored in the storage 50 until a time immediately following the next time of day signal.

The event marker signal is given the third-highest priority and this is implemented in the control logic 72 by inhibiting the EM control signal on the line 36 during the time in which the BP control signal is produced, during the time in which the T control signal is produced, and during the five seconds immediately preceding production of each T control signal. The periodicity of the T signal provides the basis for the necessary anticipation. Thus, the event marker signal normally is recorded immediately upon the patient's actuation of the event marker control 32, but if actuation occurs within five seconds before a time of day signal, generation of the event marker signal will be delayed until after the time of day signal has been recorded and until after the blood pressure signal, if any, has been recorded.

The lowest priority is assigned to the ECG signal and this is accomplished by operation of the multiplexer 46, which when controlled by the MX control signal on the line 74 does not pass the ECG signal when one of the other signals is being recorded.

The multiplexer 46 assures that only one signal is applied to the recording system 76 for recording on the second track of the tape 78.

FIG. 3 is a block diagram of the decoder system of the present invention. The tape 78 recorded as described above, is inserted into the playback system 80 to permit the signals recorded thereon to be converted into an electrical played-back signal. The played-back signal typically includes several types of non-concurrent pulse coded signals interposed between segments of a continuous ECG signal. The pulse coded signals include the blood pressure signal, the event marker signal, and the time of day signal described above. The playback system 80 is part of the electrocardiographic computer described in U.S. Pat. No. 4,006,737 and 4,073,011, referred to above.

As described in those patents, the playback system 80 includes a tachometer 82 which indicates how much tape has been played. The tachometer 82 includes an optical pickoff which is connected to a capstan driven by the tape as it moves, so that the motion of the tape produces a series of pulses produced at a rate proportional to the speed of the tape. In a preferred embodiment of the invention, the pulses produced when the tape is moving forward are 90° out of phase with the pulses produced when the tape is moving backward. The pulses produced by the tachometer 82 are referred to herein as the increment/decrement signal on the line 84; its use will be described below.

The electrical played-back signal on the line 86 is fed to a set of three decoders, each of which functions to identify one type of pulse coded signals included within the played-back signal.

Thus, for example, the blood pressure signal decoder signal 88 includes circuitry which responds only to the presence of the coded blood pressure signal in the played-back signal. Specifically, the blood pressure signal decoder system 88 recognizes the blood pressure signal by the fact that the blood pressure signal consists of a one-eighth-second perambLe and postamble along with sixteen bi-phase mark coded binary digits transmitted at a rate of 16 Hz. If such a signal is recognized, the blood pressure signal decoder system 88 transmits the verified blood pressure signal to the multiplexer 92 via the line 94, transmits the blood pressure data to the blood pressure display 90, and transmits a BP valid signal to the multiplexer 92 via the line 96.

Likewise, the event marker signal decoder system 98 recognizes the presence in the played-back signal of the coded event marker signal which consists of eight cycles at a frequency of 8 Hz. Upon recognizing the presence of such a signal in the incoming data, the event marker signal decoder system 98 transmits the verified EM signal via the line 100 to the multiplexer 92. The entire played-back signal is presented to the multiplexer 92 from the line 102, but it must be remembered that that ECG signal is not present on the line 102 when the verified EM signal is present on the line 100.

The decoding of the time of day signal is performed by the time of day signal decoder system 104. The decoder 106 receives the time of day signal from the line 86 and converts it from serial bi-phase mark code to a binary form suitable for use by the other portions of the time of day signal decoder system 104. The decoder 106 transfers the binary coded signal into a storage shift register 108 for temporary storage while certain tests are performed on the stored signal. One of these tests is a check of the parity bit of the stored signal to determine whether it has the correct parity; that is, whether it includes an even number of "ones." This test is performed by the parity check circuit 110. A bit counter 112 determines whether the tentatively identified time of day signal includes the correct number of bits, namely fourteen bits in a preferred embodiment.

It is recalled that the time of day signal in addition to its specific perambLe and postamble includes fourteen bits of data at a frequency of 21.33 Hz. The tape speed error detector 114 tests the tentatively identified time of day signal to determine if the pulses occur within it at the frequency of 21.33 Hz. To accomplish this, a clock 116 is provided to feed timing pulses to the tape speed error detector for comparison with the data pulses. If the data pulses differ from the correct frequency by more than a specified amount, the tape speed error detector 114 produces a tape speed error signal on the line 118. This signal is plotted on the chart and also is applied to the visual error indicator 119, which in a preferred embodiment is a red light. When the validity logic circuit 120 has received confirmatory signals from the parity check circuit 110, from the bit counter 112 and from the tape speed error detector 114, the validity logic produces a "valid" signal on the line 122 which clocks the time of day signal stored in the storage shift register 108 into the time of day counter register 124, displacing whatever number previously existed in the counter register 124. In the event the tape being played was produced on earlier equipment which did not have the capability of recording the time of day on the tape, the time of day must be manually set into the time of day counter register 124 by the operator.

In accordance with the present invention, the verified time of day in the counter register 124 is continually updated by the increment/decrement signal on the line 84 produced by the tachometer 82. The verified time of day signal in a preferred embodiment is produced each minute on the minute, while the increment/decrement signal is produced each second. Thus, according to the present invention, the tachometer signals are used for short term updating of the verified time of day, and this method is accurate and advantageous where the time interval between successive time of day signals is relatively short. The time of day signal stored in the counter register 124 is applied to the time of day display 126 for producing a visual display of the time and is also supplied to the printer 128 which prints the time of day on the chart.

The increment/decrement signal on the line 84 is also fed to the counter 130 which reduces the frequency of the signal and produces pulses spaced five seconds apart on the line 132. These pulses are applied to the plotter 134 and are recorded on the chart 136.

The multiplexer 92 operates under control of the BP valid signal on the line 96 to pass the verified BP signal on the line 94 to the charter 134. In the absence of the BP valid signal on the line 96, the multiplexer 92 normally passes the signals on the line 103 to the plotter 134. As was noted above, the signal on the line 103 is the ECG signal, except when that signal is interrupted by a verified EM signal. The output of the multiplexer 92 on the line 138 thus consists of the decoded and verified data and is applied to one channel of the plotter 134 in a preferred embodiment.

The tachometer pulses on the line 132 are applied to another channel of the plotter along with the tape speed error signal on line 118. The verified time of day signal is applied to the printer 128 as well as to the data channel of the plotter 134. The printer 128 prints the time of day along the edge of the chart every five seconds.

The time of day signals plotted on the chart 136 are known to have been generated at equal one-minute intervals. If the spacing on the chart between successive time of day signals does not correspond to one minute, the error could lie in the recording speed, the playback speed, or the plotter speed. It is recognized that a playback speed error of appropriate size and sense can compensate for a recording speed error. It this occurs, or if both the recording and playback speed errors are zero, no tape speed error signal will be produced on the line 118, and it will be recognized that the indicated speed error is in the plotter.

In a preferred embodiment, the duration of the tape speed error signal on the line 118 is controlled by the clock 116, and the plotted tape speed error signal on the chart is affected only by the plotter speed error. Thus, the plotter speed error can be determined by the spacing on the chart between the beginning and the end of th tape speed error signal.

The spacing on the chart between successive tachometer pulses produced on the line 132 by the tachometer 82 should correspond to a nominal time of five seconds. The plotted tachometer signals are affected by the playback speed error and by the plotter speed error. Thus, the recording speed error can be determined by comparing the indicated error in the plotted time of day signals with the indicated error in the plotted tachometer pulse signals.

When the tape speed error signal is present on the line 118, the playback speed error can be determined by comparing the indicated error in the plotted tachometer pulses with the charter speed error obtained from the plotted tape speed error signal.

When the tape speed error signal is not present on the line 118, the indicated error in the plotted time of day signals is attributable solely in the plotter speed error. In this event, the playback speed error, if it is present, can be determined by comparing the indicated error from the plotted tachometer pulses with the indicated error obtained from the plotted time of day pulses. The recording speed error in this case is equal in magnitude but opposite in sense from the playback speed error.

Thus, it can be seen that the recording and playback systems of the present invention include means to enable the determination of recording speed error, playback speed error and plotter speed error.

Figure 4:
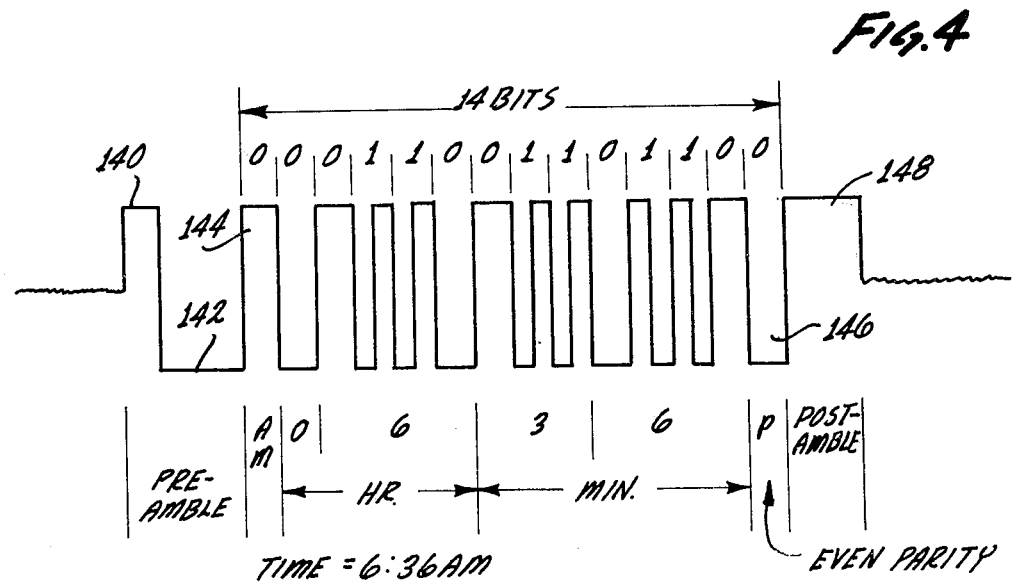
FIG. 4 is a diagram showing a time of day signal encoded in accordance with the present invention.

FIG. 4 is a diagram showing the encoded time of day signal versus time. The signal is coded in phase mark format; each bit of data is assigned one of the successive time intervals, and if the bit is a "zero," there is no transition of the signal during the interval, but if the bit is a "one," the signal makes a transition at approximately the center of the interval.

As may be seen in FIG. 4, the encoded time of day signal includes an initial pulse 140 followed by a two-bit blank 142 to produce a characteristic three-bit preamble. The signal in the preamble is quite strong and blanks out any noise that may be present, by semi-saturating the recording.

The preamble is followed by the time of day data with the bits produced at a rate of 21.33 Hz. The first data bit 144 is an a.m./p.m. indicator. This is followed by five bits which represent the hour, which in turn is followed by seven bits which represent the minute of the time of day. The final bit is a parity check bit 146 whose value is determined during the encoding of the signal. If the time of day data includes an even number of "ones," the value of the parity bit is determined to be "zero," but if the data contains an odd number of "ones," the value of the parity bit is determined to be "one." This has the effect of causing the time of day data including the parity bit to always have an even number of "ones."

The fourteen bits comprising the time of day signal are always followed by a two-bit postamble 148, which is always at a high level because the signal includes an even number of bits.

The unique features of the time of day code format, such as its short preamble and postamble, as well as the inclusion of a parity check bit, are highly advantageous in identifying and verifying the time of day signal. The inclusion of a time of day signal recorded on the same track with the ECG, blood pressure, and event marker signals results in a considerable improvement in the accuracy with which the time of occurrence of various cardiac events can be determined, since the cumulative effect of speed errors is eliminated. In accordance with the present invention, if the time of day signal is interrupted, or is not present on the tape at all, the decoder can still update the time of day through the use of a tachometer. The tachometer-determined time is overruled by the time of day signal when the latter is present.

Thus, there has been described a system for recording on a single track in a magnetic tape a channel of ECG signals interrupted intermittently by time of day signals, blood pressure signals and event marker signals. The playback and decoding apparatus described above includes means for recovering these four types of signals recorded on the same track and for positively identifying each type of signal. Because the intermittent signals are recorded in pulse coded form, a high degree of noise immunity is obtained, along with greatly enhanced dynamic range compared with analog recording.

The system of the present invention is fully compatible with existing equipment so that tapes made on existing equipment can be played back on the equipment of the present invention, and so that tapes made on the present invention can be played back on existing playback equipment. This feature is of considerable commercial importance.

In accordance with the present invention, the recording speed errors, the playback speed errors and plotter speed errors can all be identified and measured from the signals plotted on the chart. This feature is extremely useful for trouble-shooting and fine tuning of the system.

The foregoing detailed description is illustrative of the preferred embodiment of the invention, but it is to be understood that additional embodiments will be obvious to those skilled in the art. The embodiments described herein, together with those additional embodiments are considered to be within the scope of the invention.

What is claimed is:

1. A tape recorder for use in ambulatory monitoring of a cardiac patient, said tape recorder having recording head means for recording on a single track in a tape an ECG signal obtained continuously from a patient, and recording on the same single track several intermittent signals including blood pressure signal received intermittently from a portable blood pressure measuring device affixed to the patient, an event marker signal generated in response to actuation of an event marker control from time to time by the patient, and a periodic time of day signal, said tape recorder comprising in combination:

recording means operatively associated with the tape and responsive to an applied electrical signal for recording the applied electrical signal on a single track in the magnetic tape;

multiplexer means connected to said recording means and providing to said recording means the applied electrical signal to be recorded, the latter including an ECG signal and an intermittent signal selected by said multiplexer means under control of an applied MX control signal from a set of signals including an encoded time of day signal, an encoded blood pressure signal, and an encoded event marker signal;

time of day encoder means for generating and storing an encoded time of day signal representing the time of day, said time of day encoder means connected to said multiplexer means and providing said encoded time of day signal to said multiplexer means under control of an applied T control signal;

blood pressure encoder means to which the blood pressure signals received intermittently from the blood pressure measuring device are applied for converting the blood pressure signals into a form suitable for storage, for storing the converted blood pressure signals, and in response to an applied BP control signal to read out the stored converted blood pressure signals and to encode them into a predetermined format, said blood pressure encoder means connected to said multiplexer means and providing said encoded blood pressure signals to said multiplexer means;

event marker signal generator means for generating an encoded event marker signal having a predetermined format in response to an EM control signal applied after the patient has actuated the event marker control, said event marker signal generator means connected to said multiplexer means and providing said encoded event marker signal to said multiplexer means;

control logic means connected to said time of day encoder means for generating and providing to said time of day encoder means said applied T control signals, connected to said blood pressure encoder means for generating and providing thereto said applied blood pressure control signals, connected to said event marker signal generator means for generating and providing thereto said applied EM control signal, and connected to said multiplexer means and generating and providing to said multiplexer means said applied MX control signal for controlling the selection by said multiplexer means from said set of signals of an intermittent signal to be recorded.

2. The tape recorder of claim 1 wherein said control logic means is connected to said time of day encoder means and generates said BP control signal in predetermined time relationship to the T control signal to enable readout of said stored converted blood pressure signals only during an interval of time following termination of the T control signal so that each intermittently received blood pressure signal is recorded after the recording of the time of day signal next following receipt of the blood pressure signal.

3. The tape recorder of claim 2 wherein said control logic means anticipates production of each T control signal and generates said EM control signal in predetermined time relationship to the anticipated T control signal and in relation to said BP control signal to postpone generation of said encoded event marker signal to prevent it from being presented to said multiplexer means concurrently with an encoded time of day signal and to prevent it from being presented to said multiplexer means concurrently with an encoded blood pressure signal.

4. The tape recorder of claim 1 wherein said time of day encoder means further comprise a clock, and wherein said clock is connected to said control logic means and provides clock signals to said control logic means.

5. The tape recorder of claim 1 further comprising time set logic means connected to said time of day encoder means and operable under control of an operator to enter into said time of day encoder means signals representative of a selected time of day.

6. The tape recorder of claim 1 further comprising a time display connected to said time of day encoder means and providing a visual indication of the time of day stored in said time of day encoder means.

7. The tape recorder of claim 1 wherein said encoded time of day signal is updated every minute by said time of day encoder means.

8. The tape recorder of claim 1 wherein said encoded time of day signal is provided to said multiplexer means each minute on the minute by said time of day encoder means.

9. The tape recorder of claim 1 wherein said recording means record said encoded time of day signal on the tape at precisely determined equal intervals of time in the same single track on which said recording means record the ECG signal, said encoded blood pressure signal and said encoded event marker signal.

10. The tape recorder of claim 1 wherein said event marker signal generator generates an encoded event marker signal consisting of eight consecutive cycles at a rate of 8 cycles per second.

11. The tape recorder of claim 1 wherein said blood pressure encoder means further comprise an encoder for encoding the stored converted blood pressure signals into a predetermined format.

12. The tape recorder of claim 1 wherein said time of day encoder means further comprise an encoder for encoding the generated time of day signals into a predetermined format.

13. The tape recorder of claim 1 further comprising a time-shared encoder for encoding the stored converted blood pressure signals into a predetermined format and for encoding the generated time of day signals into a predetermined format.

14. The tape recorder of claim 1 wherein said recording means record the time of day signal on the same track of the tape that the ECG signal is recorded on, and wherein said time of day encoder means generates an encoded time of day signal having a serial pulse code form including a 3-bit preamble, a parity checking bit, and a 2-bit postamble.

15. The tape recorder of claim 1 wherein said recording means record the encoded event marker signal on the same track of the tape that the encoded time of day signal is recorded on.

16. The tape recorder of claim 15 wherein the encoded event marker signal generated by said event marker signal generator consists of a burst of a predetermined number of pulses at a predetermined pulse rate.

17. The tape recorder of claim 1 wherein said recording means record said encoded blood pressure signal and said encoded time of day signal on the same track in the tape.

18. The tape recorder of claim 17 wherein the encoded event marker signal generated by said event marker signal generator consists of a burst of a predetermined number of pulses at a predetermined pulse rate.

19. The tape recorder of claim 1 wherein the blood pressure signals obtained intermittently from the blood pressure measuring device are in serial bi-phase mark format, and wherein said blood pressure encoder means further comprise register means for converting the obtained blood pressure signals into serial binary format and for storing the converted signals, and wherein said blood pressure encoder encodes the stored serial binary signals into serial bi-phase mark format before providing the encoded signals to said multiplexer means.

20. The tape recorder of claim 1 wherein said time of day encoder means generates said encoded time of day signal in phase mark code format including a 3-bit preamble, a parity checking bit and a 2-bit preamble.

21. A decoder system for use in analyzing tapes recorded during ambulatory monitoring of cardiac patients, wherein several types of non-concurrent pulse coded signals are recorded along with a continuous ECG signal on a single track in the tape, said decoder system identifying the pulse coded signals on the basis of their formats and comprising in combination;

playback means for converting the signals recorded on a single track of a tape into an electrical played-back signal which may include any of several types of non-concurrent pulse coded signals along with a continuous ECG signal, said pulse coded signals including, singly or in any combination, a blood pressure signal, an event marker signal and a time of day signal;

blood pressure signal decoder means, connected to said playback means to receive said played-back signal and to produce a verified blood pressure signal corresponding to a segment of said played-back signal only when said blood pressure signal decoder means has determined that said segment satisfies predetermined blood pressure signal criteria;

event marker signal decoder means, connected to said playback means to receive said played-back signal and to produce a verified event marker signal corresponding to a segment of said played-back signal only when said event marker signal decoder means has determined that said segment satisfies predetermined event marker signal criteria;

time of day signal decoder means connected to said playback means to receive said played-back signal and to produce a verified time of day signal corresponding to a segment of said played-back signal only when said time of day signal decoder means has determined that said segment satisifies predetermined time of day signal criteria;

tachometer means actuated by the tape when the tape moves and producing an electrical tachometer output signal indicative of the amount of motion of the tape; and, time of day storage means for storing an applied time of day signal and for updating the stored time of day signal in response to an applied increment-/decrement signal, connected to said tachometer means for receiving said electrical tachometer output signal as the applied increment/decrement signal, connected to said time of day signal decoder means for receiving said verified time of day signal, and operative to store said verified time of day signal when that signal is produced, and operative to increment and to decrement said stored time of day signal in response to said electrical tachometer output signal.

22. The decoder system of claim 21 wherein said time of day storage means further comprise means for manually setting the stored time of day.

23. The decoder system of claim 21 further comprising a printer connected to said time of day storage means to receive from the latter the updated time of day signal and to print the updated time on a chart at predetermined intervals.

24. The decoder system of claim 23 wherein said printer further comprises means for printing the characters a.m. and p.m.

25. The decoder system of claim 21 further comprising a time of day display connected to said time of day storage means to receive from the latter the updated time of day signal and to display the signal received.

26. The decoder system of claim 25 wherein said time of day display further comprises means for indicating a.m. and p.m.

27. The decoder system of claim 21 further comprising:
 a plotter for producing a trace on a chart representing the variations of an applied signal with respect to time; and
 counter means connected to said tachometer means for receiving therefrom said electrical tachometer output signal, connected to said plotter, producing a counter output signal related to said electrical tachometer output signal, and applying said counter output signal to said plotter as said applied signal.

28. A decoder system for use in analyzing tapes recorded during ambulatory monitoring of cardiac patients, wherein several types of non-concurrent pulse coded signals and a continuous ECG signal are recorded on a single track in the tape, said decoder system identifying the pulse coded signals on the basis of their formats and comprising in combination:
 playback means for converting the signals recorded on a single track of a tape into an electrical played-back signal which may include any of several types of non-current pulse coded signals and a continuous ECG signal, said pulse coded signals including, singly or in any combination, a blood pressure signal, an event marker signal and a time of day signal;
 blood pressure signal decoder means, connected to said playback means to receive said played-back signal and to produce a verified blood pressure signal corresponding to a segment of said played-back signal only when said blood pressure signal decoder means has determined that said segment satisfies predetermined blood pressure signal criteria;
 event marker signal decoder means, connected to said playback means to receive said played-back signal and to produce a verified event marker signal corresponding to a segment of said played-back signal only when said event marker signal decoder means has determined that said segment satisfies predetermined event marker signal criteria;
 time of day signal decoder means connected to said playback means to receive said played-back signal and to produce a verified time of day signal corresponding to a segment of said played-back signal only when said time of day signal decoder means has determined that said segment satisfies predetermined time of day signal criteria;
 wherein said time of day signal decoder means further comprise a decoder connected to said playback means for receiving the played-back signal and responsive thereto to produce a decoded time of day signal; and,
 wherein said time of day signal decoder means further comprise tape speed error detector means connected to said decoder to receive from it said decoded time of day signal and operative to determine the amount by which the pulse repetition frequency of the decoded time of day signal deviates from a predetermined pulse repetition frequency criterion and to generate a tape speed error signal when the amount of the deviation exceeds a predetermined limit.

29. The decoder system of claim 28 further comprising a plotter connected to said tape speed error detector means for marking a graphic indication on a chart in response to said tape speed error signal.

30. The decoder system of claim 29 wherein said graphic indication is a burst of a predetermined number of pulses of a predetermined repetition frequency.

31. The decoder system of claim 28 further comprising a visual error indicator connected to said tape speed error detector means and responsive to said tape speed error signal to produce a visual error indication.

32. A decoder system for use in analyzing tapes recorded during ambulatory monitoring of cardiac patients, wherein several types of non-concurrent pulse coded signals are recorded along with a continuous ECG signal on a single track in the tape, said decoder system identifying the pulse coded signals on the basis of their formats and comprising in combination:
 playback means for converting the signals recorded on a single track of a tape into an electrical played-back signal which may include any of several types of non-concurrent pulse coded signals along with a continuous ECG signal, said pulse coded signals including, singly or in any combination, a blood pressure signal, an event marker signal and a time of day signal;
 blood pressure signal decoder means, connected to said playback means to receive said played-back signal and to produce a verified blood pressure signal corresponding to a segment of said played-back signal only when said blood pressure signal decoder means has determined that said segment satisfies predetermined blood pressure signal criteria;
 event marker signal decoder means, connected to said playback means to receive said played-back signal and to produce a verified event marker signal corresponding to a segment of said played-back signal only when said event marker signal decoder means has determined that said segment satisfies predetermined event marker signal criteria; and,
 time of day signal decoder means connected to said playback means to receive said played-back signal and to produce a verified time of day signal corresponding to a segment of said played-back signal only when said time of day signal decoder means has determined that said segment satisfies predetermined time of day signal criteria.

33. The decoder system of claim 32 wherein said verified time of day signal includes an a.m./p.m. signal component.

34. The decoder system of claim 32 wherein said time of day signal decoder means further comprise a bit counter operative to generate a bit count valid signal when the played-back signal consists of a burst of a predetermined number of pulses.

35. The decoder system of claim 32 wherein said time of day signal decoder means further comprise parity check means operative to generate a parity valid signal when the played-back signal has a predetermined parity.

36. The decoder system of claim 32 wherein said predetermined event marker signal criteria include a predetermined number of pulses occurring at a predetermined pulse repetition rate.

37. The decoder system of claim 32 wherein said predetermined blood pressure signal criteria include a predetermined number of data bits occurring in a time interval of predetermined length.

38. The decoder system of claim 32 wherein said predetermined time of day signal criteria include an initial pulse followed by a two-bit preamble, thirteen bits of data, followed by a parity bit, followed by a two-bit postamble.

39. The decoder system of claim 32 further comprising:
   a plotter for producing a trace on a chart representing the variations of an applied signal with resect to time; and,
   multiplex means connected to said playback means and receiving said ECG signal therefrom, connected to said blood pressure signal decoder means to receive said verified blood pressure signal and a BP valid signal therefrom, connected to said event marker signal decoder means to receive said verified event marker signal therefrom, connected to said plotter for supplying to it said applied signal, operative in response to said BP valid signal to pass said verified blood pressure signal to said plotter as said applied signal, and operative in the absence of said BP valid signal to pass said ECG signal and said verified event marker signal to saidd plotter as said applied signal.

40. In a system in which a data signal is recorded on a tape, then later played back and applied to a plotter to produce a chart on which the data signal is plotted versus time and on which a specific distance along the time axis is intended to represent a corresponding specific time interval, a method for determining recorder speed error, playback speed error and plotter speed error, said method comprising the steps of:

(a) recording on the tape time of day signals known to be generated at precisely determined intervals of time;
(b) playing back and plotting on the chart the recorded time of day signals;
(c) generating a tachometer signal as the tape is played back each time the tape has moved a predetermined distance plotter andd plotted versus time on the chart;
(d) producing a plot on the chart of the tachometer signals versus time by applying the tachometer signals to the plotter;
(e) generating a tape speed error signal as the tape is played back when the time between successive played back time of day signals deviates by more than a specified amount from the precisely determined intervals of time at which the time of day signals were generated, said tape speed error signals being indicative of a net error in the recordiing and playback tape speeds and consisting of a signal generated with a known duration, applied to the plotter and plotted versus time on the chart;
(f) determining the plotter speed error, when said tape speed error signal is not being generated, from the distance between successive plotted time of day signals;
(g) determining the plotter speed error, when said tape speed error signal is being generated, from the distance between the beginning and end of the tape speed error signal;
(h) determining the playback speed error from the spacing between successive tachometer signals plotted on the chart and the plotter speed error;
(i) determining the recorder speed error from the spacing on the chart between successive time of day signals plotted on the chart and the playback speed error determined in step (h).

41. The method of claim 40 wherein the data signal which is recorded on the tape is an ECG signal.

42. The method of claim 40 wherein said time of day signal and the data signal are recorded on the same track on the tape.

* * * * *